US012622646B2

(12) United States Patent
Kwon et al.

(10) Patent No.: US 12,622,646 B2
(45) Date of Patent: May 12, 2026

(54) METHOD OF EXTRACTING REPRESENTATIVE WAVEFORM OF BIO-SIGNAL AND APPARATUS FOR ESTIMATING BIO-INFORMATION

(71) Applicant: SAMSUNG ELECTRONICS CO., LTD., Suwon-si (KR)

(72) Inventors: Ui Kun Kwon, Hwaseong-si (KR); Young Soo Kim, Seoul (KR); Chang Soon Park, Chungju-si (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1124 days.

(21) Appl. No.: 17/671,926

(22) Filed: Feb. 15, 2022

(65) Prior Publication Data

US 2023/0139441 A1 May 4, 2023

(30) Foreign Application Priority Data

Oct. 28, 2021 (KR) ........................ 10-2021-0145514

(51) Int. Cl.
*A61B 5/00* (2006.01)
*A61B 5/021* (2006.01)
(52) U.S. Cl.
CPC ........ *A61B 5/7221* (2013.01); *A61B 5/02108* (2013.01); *A61B 5/7203* (2013.01)

(58) Field of Classification Search
CPC . A61B 5/7221; A61B 5/02108; A61B 5/7203; A61B 5/02438; A61B 5/352; A61B 5/681; A61B 5/6815; A61B 5/7235; A61B 5/7246; A61B 5/02416; A61B 5/7225
See application file for complete search history.

(56) References Cited

U.S. PATENT DOCUMENTS

| | | | |
|---|---|---|---|
| 6,358,201 B1 * | 3/2002 | Childre | ................ A61B 5/0245 |
| | | | 600/300 |
| 6,612,382 B2 | 9/2003 | King | |
| 6,714,804 B2 | 3/2004 | Al-Ali et al. | |

(Continued)

FOREIGN PATENT DOCUMENTS

| KR | 2003-0081903 A | 10/2003 |
|---|---|---|
| KR | 10-2004-0067240 A | 7/2004 |

(Continued)

OTHER PUBLICATIONS

Office Action issued on Oct. 10, 2023 by the Korean Patent Office in corresponding KR patent application No. 10-2021-0145514.

*Primary Examiner* — Tung S Lau
(74) *Attorney, Agent, or Firm* — Sughrue Mion, PLLC

(57) ABSTRACT
A method of extracting a representative waveform of a bio-signal includes receiving an input of the bio-signal; dividing the bio-signal into a plurality of sub-signals; selecting at least one sub-signal for extracting a representative waveform from among the divided sub-signals; extracting a representative waveform by using the at least one selected sub-signal; evaluating a quality of the extracted representative waveform; and based on the representative waveform satisfying a predetermined quality criterion corresponding to the evaluation, determining that the representative waveform is a final representative waveform.

24 Claims, 16 Drawing Sheets

(56) References Cited

U.S. PATENT DOCUMENTS

| | | | |
|---|---|---|---|
| 6,905,470 | B2 | 6/2005 | Lee et al. |
| 7,613,486 | B2 | 11/2009 | Yeo et al. |
| 10,524,736 | B2 | 1/2020 | Gross |
| 10,627,783 | B2 | 4/2020 | Rothkopf et al. |
| 11,457,872 | B2 | 10/2022 | Jang et al. |
| 2018/0128861 | A1 | 5/2018 | Jang |
| 2018/0300997 | A1* | 10/2018 | Chen ..................... G06F 3/167 |
| 2020/0221963 | A1 | 7/2020 | Jang |
| 2021/0000429 | A1 | 1/2021 | Yoon et al. |
| 2021/0007615 | A1 | 1/2021 | Jang et al. |
| 2023/0000444 | A1 | 1/2023 | Jang et al. |

FOREIGN PATENT DOCUMENTS

| | | |
|---|---|---|
| KR | 10-2011-0087501 A | 8/2011 |
| KR | 10-1593412 B1 | 2/2016 |
| KR | 10-2018-0050947 A | 5/2018 |
| KR | 10-2019-0065115 A | 6/2019 |
| KR | 10-2020-0088700 A | 7/2020 |
| KR | 10-2021-0004376 A | 1/2021 |
| KR | 10-2021-0007368 A | 1/2021 |
| KR | 10-2021-0073260 A | 6/2021 |

* cited by examiner

METHOD OF EXTRACTING REPRESENTATIVE WAVEFORM OF BIO-SIGNAL AND APPARATUS FOR ESTIMATING BIO-INFORMATION

CROSS-REFERENCE TO RELATED APPLICATION(S)

This application claims priority from Korean Patent Application No. 10-2021-0145514, filed on Oct. 28, 2021, in the Korean Intellectual Property Office, the entire disclosure of which is incorporated herein by reference for all purposes.

BACKGROUND

1. Field

The disclosure relates to estimating bio information, and in particular to a method of extracting a representative waveform of a bio-signal, and an apparatus for estimating bio-information based on the extracted representative waveform.

2. Description of the Related Art

Due to the aging population, soaring medical costs, and a lack of medical personnel for specialized medical services, research is being actively conducted on IT-medical convergence technologies, in which IT technology and medical technology are combined. Particularly, monitoring of the health condition of the human body is not limited to medical institutions, but is expanding to mobile healthcare fields that may monitor a user's health condition anywhere and anytime in daily life at home or office. Typical examples of bio-signals, indicating the health condition of individuals, include an electrocardiography (ECG) signal, a photoplethysmogram (PPG) signal, an electromyography (EMG) signal, etc., and various bio-signal sensors have been developed to measure these signals in daily life. Particularly, a PPG sensor may estimate blood pressure of a human body by analyzing a shape of pulse waves which reflect cardiovascular status and the like.

According to studies on the PPG signal, the whole PPG signal is a summation of a propagation wave propagating from the heart to peripheral parts of a body and reflection waves returning from the peripheral parts of the body. Information for use in estimating blood pressure can be acquired by extracting various features related to propagation waves or reflection waves. However, if the quality of a bio-signal is degraded due to arrhythmia or motion noise in heartbeat, the accuracy in estimating blood pressure may be reduced.

SUMMARY

According to an aspect of the disclosure, a method of extracting a representative waveform of a bio-signal may include: receiving an input of the bio-signal; dividing the bio-signal into a plurality of sub-signals; selecting at least one sub-signal for extracting a representative waveform from among the divided sub-signals; extracting a representative waveform by using the at least one selected sub-signal; evaluating a quality of the extracted representative waveform; and based on the representative waveform satisfying a predetermined quality criterion corresponding to the evaluation, determining that the representative waveform is a final representative waveform.

The dividing of the bio-signal into the plurality of sub-signals may include dividing the bio-signal into the sub-signals based on units of beats.

The selecting of the at least one sub-signal may include selecting a predetermined number of sub-signals or sub-signals in a predetermined time interval.

The selecting of the at least on sub-signal may include selecting a plurality of sub-signals. The extracting of the representative waveform may include: setting a reference point in each of the plurality of selected sub-signals; and overlapping the plurality of selected sub-signals based on the set reference point in each of the plurality of selected sub-signals.

The setting of the reference point may include setting, as the reference point, at least one of a minimum point, a maximum point, a maximum slope point, and a tangent intersection point of the waveform one of the plurality of selected sub-signals.

The overlapping of the plurality selected sub-signals may include overlapping the plurality of selected sub-signals after normalizing the plurality of selected sub-signals to a same size.

The selecting of the at least on sub-signal may include selecting a plurality of sub-signals. The extracting of the representative waveform comprises extracting the representative waveform by applying weights to the plurality of selected sub-signals, and then overlapping the weighted sub-signals.

The extracting of the representative waveform may include: in response to the representative waveform being extracted, determining whether a number of iterations is satisfied; based on the number of iterations not being satisfied, adjusting the weights; extracting a new representative waveform by applying the adjusted weights to the plurality of selected sub-signals; and overlapping the sub-signals having the adjusted weights.

The determining whether the number of iterations is satisfied may include: determining that the number of iterations is satisfied based on a similarity between a representative waveform in a current iteration and a representative waveform in a previous iteration being greater than or equal to a first predetermined threshold value; and determining that the number of iterations is satisfied based on a difference between a quality evaluation result of the plurality of selected sub-signals in the current iteration and a quality evaluation result of the plurality of selected sub-signals in the previous iteration being less than or equal to a second predetermined threshold value.

The extracting of the representative waveform may further include evaluating a quality of the plurality of selected sub-signals. The adjusting of the weights may include adjusting the weights based on the quality evaluation result of the plurality of selected sub-signals.

The method may further include, in response to the quality of the sub-signals not satisfying the predetermined quality criterion, repeating the receiving of the input of the bio-signal. The selecting of the at least one sub-signal may include excluding some sub-signals selected during a previous iteration, and including some new sub-signals divided during current iteration.

The selecting of the at least one sub-signal may include excluding some sub-signals in time sequential order or in order starting from a lowest quality among the sub-signals in the previous iteration.

According to another aspect of the disclosure, an apparatus for estimating bio-information may include: a sensor configured to measure a bio-signal from an object; and a processor configured to: divide the bio-signal into a plurality of sub-signals; select at least one sub-signal for extracting a representative waveform from among the divided sub-signals; extract a representative waveform by using the at least one selected sub-signal; evaluate a quality of the extracted representative waveform; and based on the representative waveform satisfying a predetermined quality criterion corresponding to the evaluation, determine that the representative waveform is a final representative waveform.

The processor may be further configured to estimate bio-information based on the final representative waveform.

The at least one selected sub-signal may include a plurality of selected sub-signals. The processor may be further configured to set a reference point in each of the plurality selected sub-signals, and extract the representative waveform by overlapping the plurality of selected sub-signals based on the set reference point in each of the plurality of selected sub-signals.

The processor may be further configured to set, as the reference point, at least one of a minimum point, a maximum point, a maximum slope point, and a tangent intersection point of the waveform of one of the plurality of selected sub-signals.

The at least one selected sub-signal may include a plurality of selected sub-signals, the processor may be further configured to extract the representative waveform by applying weights to the plurality of selected sub-signals, and then overlapping the weighted sub-signals.

The processor may be further configured to overlap the plurality of selected sub-signals after normalizing the plurality of selected sub-signals to a same size.

Upon extracting the representative waveform, the processor may be further configured to: determine whether a number of iterations is satisfied; in response to the number of iterations not being satisfied, adjust the weights; extract a new representative waveform by applying the adjusted weights to the plurality of sub-signals; and overlap the selected sub-signals having the adjusted weights.

The processor may be further configured to: determine that the number of iterations is satisfied based on a predetermined number of times of iteration is satisfied; determine that the number of iterations is satisfied based on a similarity between a representative waveform in a current iteration and a representative waveform in a previous iteration being greater than or equal to a first predetermined threshold value; and determine that the number of iterations is satisfied based on a difference between a quality evaluation result of the at least one selected sub-signal in the current iteration and a quality evaluation result of the at least one selected sub-signal in the previous iteration being less than or equal to a second predetermined threshold value.

The processor may be further configured to evaluate a quality of the at least one selected sub-signal, and adjusts the weight based on a quality evaluation result of the at least one selected sub-signal.

In response to the quality of the sub-signals not satisfying the predetermined quality criterion, the processor may be further configured to repeatedly receive an input of the bio-signal. The processor may be further configured to exclude some sub-signals selected during a previous iteration, and includes some new sub-signals divided during a current iteration.

According to yet another aspect of the disclosure, a method of extracting a representative waveform of a bio-signal may include receiving a first input of the bio-signal; dividing the first bio-signal into a plurality of sub-signals; selecting at a plurality of sub-signals for extracting a representative waveform from among the divided sub-signals; extracting a representative waveform by using the plurality of selected sub-signals; evaluating a quality of the extracted representative waveform; based on the representative waveform satisfying a predetermined quality criterion corresponding to the evaluation, determining that the representative waveform is a final representative waveform; based on the representative waveform not satisfying the predetermined quality criterion corresponding to the evaluation: receiving a second input of the bio signal; selecting a sub-signal from the second input of the bio signal; extracting the representative waveform by using the plurality of selected sub-signals and the sub-signal from the second input of the bio signal.

BRIEF DESCRIPTION OF THE DRAWINGS

FIGS. 3 to 8B are diagrams explaining processes of extracting a representative waveform of a bio-signal according to embodiments.

Figure 1:
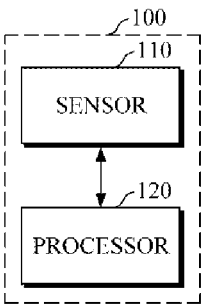
FIG. 1 is a block diagram of an apparatus for estimating bio-information according to an embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Details of example embodiments are included in the following detailed description and drawings. Advantages and features of the present disclosure, and a method of achieving the same will be more clearly understood from the following example embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the words "comprise" and "include" and variations such as "comprises," "comprising," "includes," and "including" will be understood to imply the inclusion of stated elements but not the exclusion of any other elements. Terms such as "unit" and "module" denote units that process at least one function or operation, and they may be implemented by using hardware, software, or a combination of hardware and software.

Hereinafter, embodiments of a method of extracting a representative waveform for estimating bio-information and an apparatus for estimating bio-information will be described in detail with reference to the accompanying drawings. The apparatus for estimating bio-information according embodiments may be mounted in a terminal, such as a smartphone, a tablet PC, a desktop computer, a laptop computer, etc., or may be manufactured as an independent hardware device. In this case, the independent hardware device may be a wearable device worn by an object, such as a wristwatch-type wearable device, a bracelet-type wearable device, a wristband-type wearable device, a ring-type wearable device, a glasses-type wearable device, a headband-type wearable device, etc., but is not limited thereto FIG. 1 is a block diagram showing an apparatus for estimating bio-information according to an embodiment.

Referring to FIG. 1, an apparatus 100 for estimating bio-information may include a sensor 110 and a processor 120 (or one or more processors). The sensor 110 and the processor 120 may be integrally formed with each other in a single hardware device, or may be separately formed in two or more hardware devices.

The sensor 110 may acquire a bio-signal having periodicity, i.e., bio-signal having a plurality of repetitive pulse waveforms, by continuously measuring the bio-signal from an object for a predetermined period of time. In this case, the bio-signal may be, for example, electrocardiography (ECG), photoplethysmogram (PPG), ballistocardiogram (BCG), Electromyography (EMG), impedance plethysmogram (IPG), pressure wave, video plethysmogram (VPG), etc., but is not limited thereto.

For example, the sensor 110 may include a PPG sensor for acquiring a PPG signal from an object, and the PPG sensor may include one or more light sources for emitting light onto a user's object and one or more detectors for detecting light reflected or scattered from the object. The light source may include a light emitting diode (LED), a laser diode (LD), a phosphor, etc., and may be formed as a single light source or an array of two or more light sources. The respective light sources may emit light of different wavelengths. Further, the detector may include a photodiode, a phototransistor, a complementary metal-oxide semiconductor (CMOS) image sensor, a charge-coupled device (CCD) image sensor, etc., and may be formed as a single detector or an array of two or more detectors.

The processor 120 may be electrically connected to the sensor 110. The processor 120 may control the sensor 110 in response to a request for estimating bio-information, and the sensor 110 may acquire a bio-signal from the object. The request for estimating bio-information may be input by a user or may be generated at predetermined intervals.

Upon receiving the bio-signal from the sensor 110, the processor 120 may determine a representative waveform among waveforms of the bio-signal. By using the received bio-signal itself, a filtered bio-signal obtained by filtering the received bio-signal with a low-pass filter, a high-pass filter, a band-pass filter, etc., or a bio-signal obtained by Nth order differentiation/integration of the received bio-signal, and the like, the processor 120 may determine a representative waveform of the bio-signal measured by the sensor 110. In addition, the processor 120 may determine a representative waveform of the bio-signal by using an ensemble average of PPG signals acquired by the PPG sensor, or by using an ensemble average of second derivative signals of the PPG signals.

Hereinafter, various examples of determining a representative waveform of a bio-signal will be described with reference to FIGS. 2 to 10.

Figure 2:
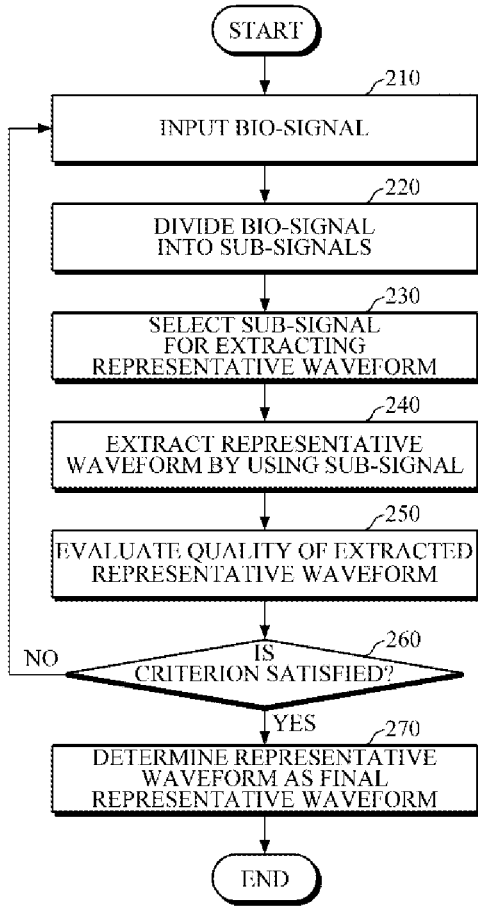
FIG. 2 is a flowchart of a method of extracting a representative waveform of a bio-signal according to an embodiment an embodiment.

FIG. 2 is a flowchart of a method of determining a representative waveform of a bio-signal according to an embodiment. FIGS. 3 to 8B are diagrams explaining each process of determining a representative waveform of a bio-signal according to embodiments.

Referring to FIG. 2, the processor 120 may receive an input of a bio-signal from an object in operation 210. For example, the processor 120 may acquire a bio-signal, having periodicity, which is measured by the sensor 110 from the object.

Figure 3:
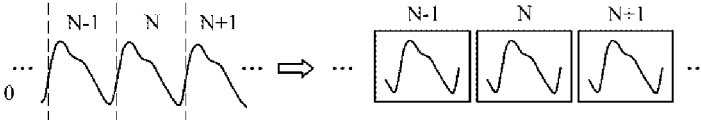

Then, the processor 120 may divide the bio-signal into a plurality of sub-signals in operation 220. For example, when a continuous PPG signal is acquired as shown in FIG. 3, the respective pulses of the PPG signal may correspond to heartbeats. The processor 120 may divide the PPG signal into sub-signals . . . , N−1, N, N+1, . . . corresponding to the respective heartbeats.

Figure 4:
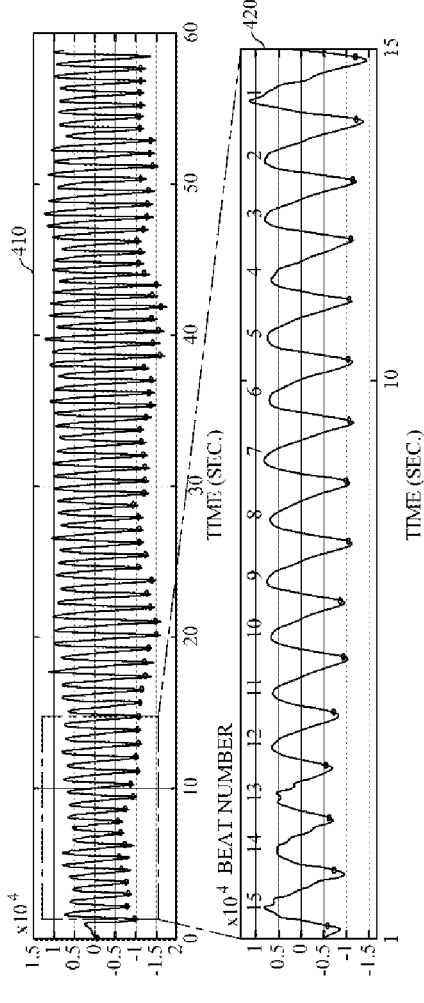

Subsequently, the processor 120 may select at least one sub-signal for extracting a representative waveform from among the divided sub-signals in operation 230. For example, the processor 120 may select a predetermined number of sub-signals or sub-signals in a predetermined time interval for extracting the representative waveform. FIG. 4 shows an example in which for generating a representative waveform, the processor 120 selects a sub-signal 420, corresponding to 15 heartbeats, in a PPG signal 410 acquired by the sensor 110. In the PPG signal acquired over time, the processor 120 may select a number of sub-signals, which corresponds to a predetermined number of beats (15 beats in the embodiment of FIG. 4) from a predetermined time point, or may select beats included in a predetermined time interval (interval of 14 seconds in the embodiment of FIG. 4) from a predetermined time point. The predetermined time point may be a time point when a threshold time elapses after the sensor 110 begins to acquire the PPG signal, or may be a time point when an amplitude of the PPG signal begins to increase to a value greater than or equal to a threshold value. Another embodiment of the predetermined time point may also be provided.

Next, the processor 120 may extract a representative waveform by using the selected at least one sub-signal in operation 240.

Figure 5:
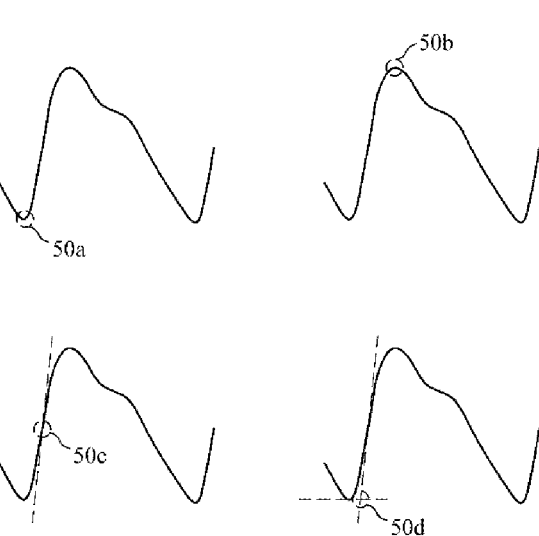

For example, the processor 120 may set a reference point in each of the sub-signals. For example, as shown in FIG. 5, the processor 120 may set, as the reference point, an initial minimum point 50a, a maximum point 50b, a maximum slope point 50c, a tangent intersection point 50d which is an intersection point of a tangent line at the initial minimum point and a tangent line at the maximum slope point, and the like, but the reference point is not limited thereto.

Figure 6A:
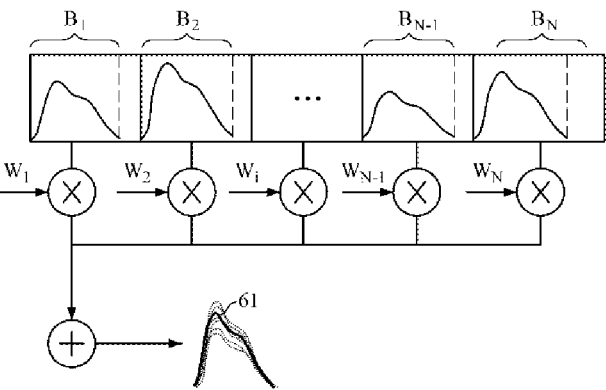
Figure 6B:
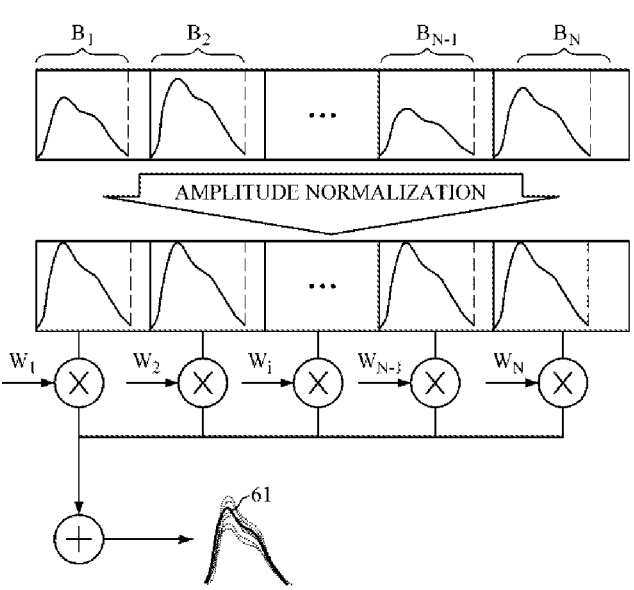

Subsequently, the processor 120 may extract a representative waveform by overlapping the selected sub-signals based on the reference point. Referring to FIG. 6A, the processor 120 may obtain a representative waveform 61 by applying weights $W_1, W_2, \ldots, W_i, \ldots, W_{N-1}$, and $W_N$, which are predetermined for the respective sub-signals $B_1, B_2, \ldots, B_{N-1}$, and $B_N$, to the respective sub-signals $B_1, B_2, \ldots, B_{N-1}$, and $B_N$ and by overlapping the sub-signals $B_1, B_2, \ldots, B_{N-1}$, and $B_N$. In this case, initial weight values applied to the respective sub-signals may be a value equally defined for the respective sub-signals, or may be values with at least some values defined differently. Then, the weights may be updated based on the quality of the respective sub-signals. An example in which the weights are updated will be described in detail below with reference to FIG. 9. Referring to FIG. 6B, the processor 120 may normalize amplitudes of the respective sub-signals $B_1$, $B_2$, . . . , $B_{N-1}$, and $B_N$ to the same size, and may obtain the representative waveform 61 by applying weights to the normalized sub-signals $B_1$, $B_2$, . . . , $B_{N-1}$, and $B_N$, and then overlapping the sub-signals. In this manner, if an abnormally large noise signal is detected as a sub-signal, the effect of a corresponding noise beat may be reduced.

The applying of weights to the respective sub-signals in the embodiments of FIGS. 6A and 6B may indicate multiplying the respective sub-signals by the weights. In this manner, the amplitudes of the sub-signals may be adjusted based on the weights, by which the respective sub-signals are multiplied.

In addition, in the embodiments of FIGS. 6A and 6B, the overlapping of the sub-signals may refer to summation (addition) of the sub-signals. That is, the processor 120 may generate a representative waveform by summation of the weighted sub-signals. In this case, a sum of amplitudes of the weighted sub-signals may correspond to an amplitude of the representative waveform. In another example, the overlapping of the sub-signals may refer to an average of the sub-signals, and the processor 120 may generate a representative waveform by using the average of the weighted sub-signals. In this case, an average value of the amplitudes of the weighted sub-signals may correspond to an amplitude of the representative waveform.

When overlapping the respective sub-signals, a reference point may be used as a reference position for the overlapping. In one embodiment, the processor 120 may overlap the respective sub-signals by summation of amplitude values which are equally spaced apart in a time axis direction from the reference point in the respective sub-signals.

Then, the processor 120 may evaluate the quality of the extracted representative waveform in operation 250.

For example, the processor 120 may evaluate the quality of the respective sub-signals by comparing the extracted representative waveform with the selected sub-signal, and may evaluate the quality of the extracted respective waveform based on the evaluation.

Figure 7A:
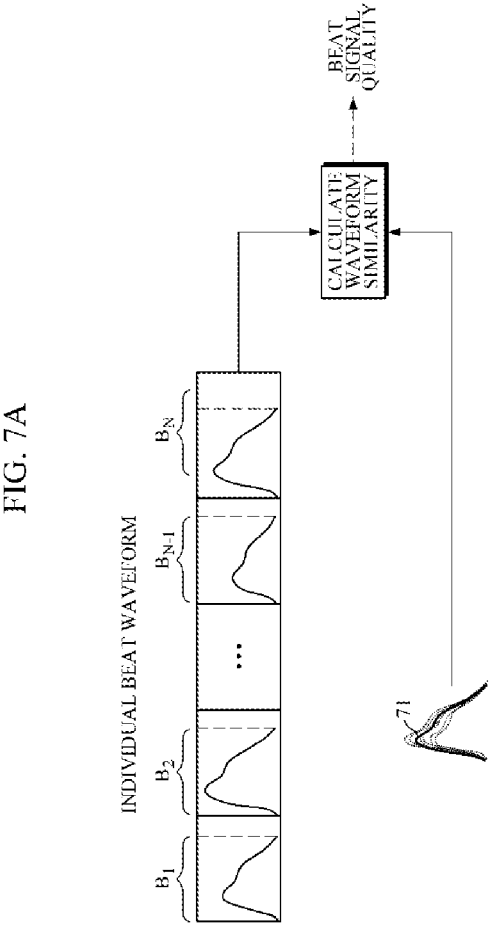
Figure 7B:
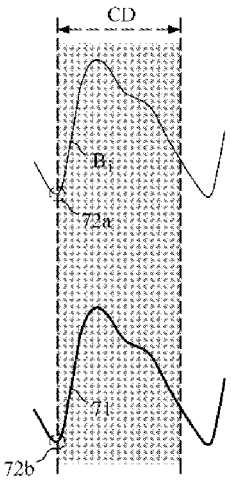

For example, as shown in FIG. 7A, the processor 120 may calculate a waveform similarity between a representative waveform 71 and the respective sub-signals $B_1$, $B_2$, . . . , $B_{N-1}$, and $B_N$, and may evaluate the quality of the respective sub-signals $B_1$, $B_2$, . . . , $B_{N-1}$, and $B_N$ based on the calculated similarity. In this case, the processor 120 may obtain the similarity value itself or a value, obtained by using a predetermined model (such as a neural network model), as quality values of the respective sub-signals. In this case, the similarity may be calculated by various methods, such as correlation coefficient, Mean Square Error (MSE), Root Mean Square Error (RMSE), and the like.

In the case where the sub-signals are divided in units of beats, the respective sub-signals may have different durations due to different heartbeats, and as a result, latter portions of the respective sub-signal waveforms may have different shapes. Accordingly, the processor 120 may calculate a similarity between the representative waveform and the respective sub-signals during a predetermined period of the sub-signals. For example, referring to FIG. 7B, instead of normalizing a length of the representative waveform 71 and the sub-signal $B_i$, to the same size, the processor 120 may calculate a similarity between the representative waveform and a waveform in a predetermined region CD which does not include the latter portion of the waveform. For example, the processor 120 may determine, as the similarity calculation region, an interval corresponding to 10% to 70% of a duration of the representative waveform, an interval corresponding to 75% of an average or a median value of durations of the sub-signals from the reference points 72a and 72b, and the like.

Then, based on quality evaluation results of the respective sub-signals, the processor 120 may calculate a statistical value, such as a mean value, a median value, standard deviation, variance, coefficient of variation, etc., of quality values of the respective sub-signals, and may evaluate the quality of the representative waveform based on the calculated statistical value. For example, the processor 120 may determine the calculated statistical value itself or a value, obtained by applying a predefined model, as the signal quality value of the corresponding representative waveform.

Subsequently, based on the evaluation result, the processor 120 may determine whether the representative waveform satisfies a predetermined quality criterion in operation 260, and if the representative waveform satisfies the predetermined quality criterion, the processor 120 may determine the representative waveform as a final representative waveform in operation 270. For example, if the quality of the representative waveform is greater than or equal to a predetermined threshold value (e.g., an average of the qualities of the sub-signals being 0.65), the processor 120 may determine that the quality is good and may determine the representative waveform as a final representative waveform. Based on the evaluation result, if the quality of the representative waveform does not satisfy the predetermined threshold value, the processor 120 may repeat operation 210 of receiving an input of a bio-signal, in which by excluding some of the sub-signals selected during the previous iteration, the processor 120 may select sub-signals including some of new sub-signals divided during the current iteration. For example, the processor 120 may exclude some of the sub-signals in time sequential order or in order starting from the lowest quality among the sub-signals in the previous iteration.

Figure 8A:
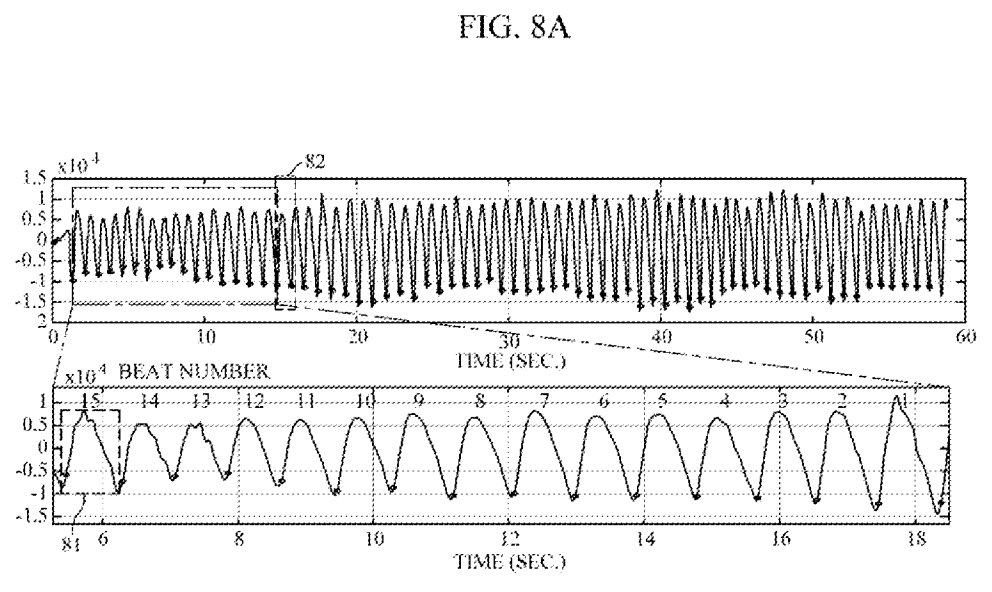
Figure 8B:
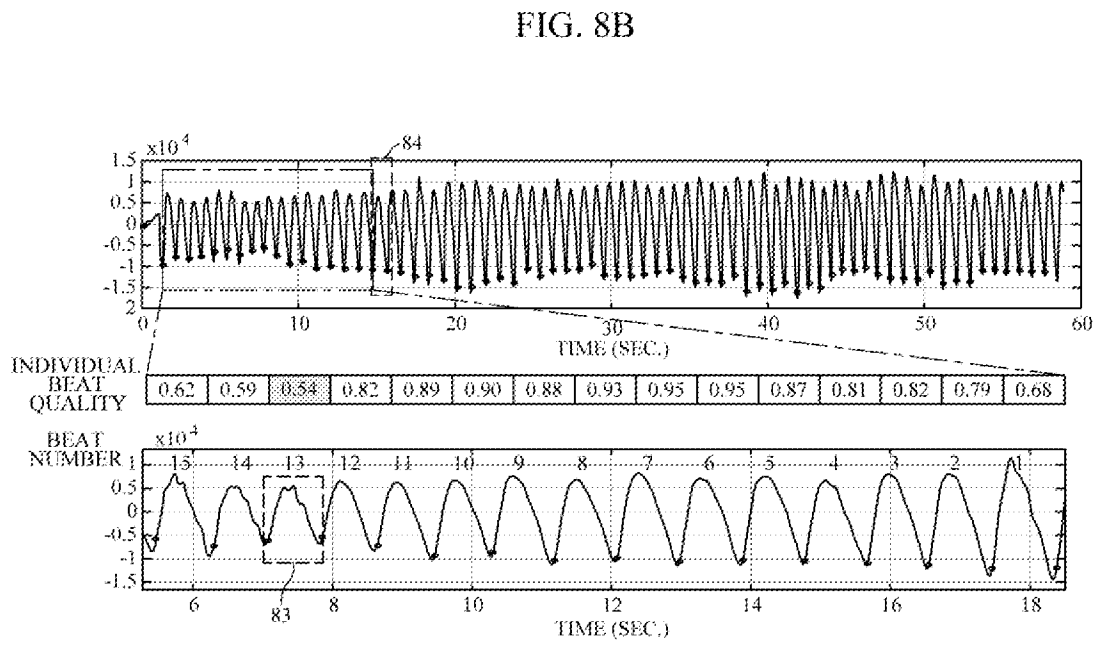

For example, if the representative waveform, generated based on a predetermined number of sub-signals or sub-signals in a predetermined time interval, does not satisfy a quality criterion, the processor 120 may further acquire one periodic signal and may generate a representative waveform again. In this case, the processor 120 may select sub-signals for use in generating a representative waveform from among the predetermined number of existing sub-signals or the existing sub-signals in the predetermined time interval, and newly acquired sub-signals. As shown in FIG. 8A, by excluding a first sub-signal 81, which is first measured using First-In First-Out (FIFO), and by adding a newly acquired sub-signal 82, the processor 120 may select sub-signals to be overlapped. Alternatively, as shown in FIG. 8B, the processor 120 may evaluate the quality of the respective sub-signals, and by excluding a sub-signal 83 having the lowest signal quality (e.g., 0.54), and by adding a newly measured sub-signal 84, the processor 120 may select a sub-signal to be overlapped.

Figure 9:
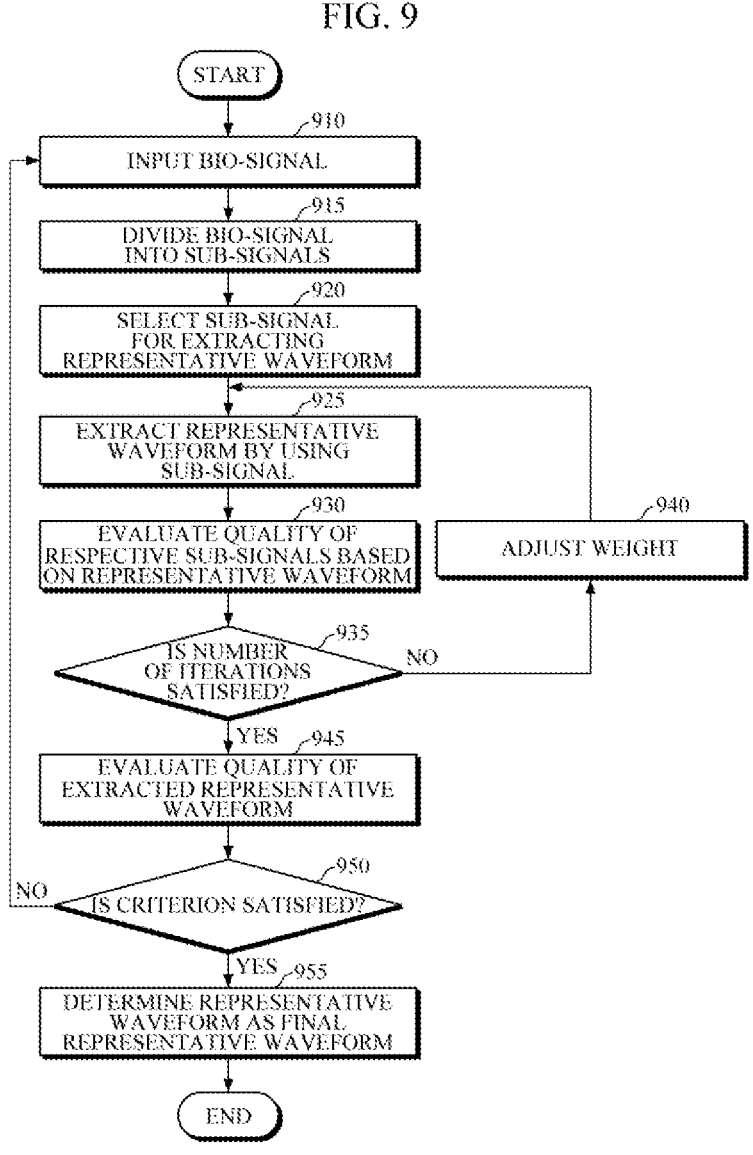
FIG. 9 is a flowchart of a method of extracting a representative waveform of a bio-signal according to an embodiment.

FIG. 9 is a flowchart of a method of determining a representative waveform of a bio-signal according to another embodiment. Portions described above will be briefly described below in order to avoid redundancy.

Referring to FIG. 9, the processor 120 may receive an input of a bio-signal from an object in operation 910. For example, the processor 120 may acquire a bio-signal, having periodicity, which is measured by the sensor 110 from the object.

Then, the processor 120 may divide the bio-signal into a plurality of sub-signals in operation 915. For example, the processor 120 may divide the continuous bio-signal into sub-signals in units of beats.

Subsequently, the processor 120 may select at least one sub-signal for extracting a representative waveform from among the divided sub-signals in operation 920. For example, the processor 120 may select a predetermined number of sub-signals or sub-signals in a predetermined time interval for extracting the representative waveform.

Next, the processor 120 may extract a representative waveform by using the selected sub-signals in operation 925. For example, by setting a reference point in each of the sub-signals, by applying weights to the selected sub-signals, and then by overlapping the sub-signals based on the set reference point, the processor 120 may extract one representative waveform. In this case, an initial weight value applied to the respective sub-signals may be a fixed value (e.g., 1) equally defined for the respective sub-signals, or may be values with at least some values defined differently.

Then, the processor 120 may evaluate the quality of the respective sub-signals in operation 930 by using the representative waveform extracted in operation 925. For example, the processor 120 may calculate a waveform similarity between the representative waveform and the respective sub-signals, and may evaluate the quality of the respective sub-signals based on the similarity. For example, the processor 120 may obtain a similarity value itself of the respective sub-signals, or a value obtained by using a predetermined model, as the quality values of the respective sub-signals.

Subsequently, the processor 120 may determine whether a number of iterations for extracting the representative waveform is satisfied in operation 935. For example, if a number of a current iteration satisfies a predefined reference value, the processor 120 may determine that the number of iterations is satisfied, and if the number of iterations is less than the predefined reference value, the processor 120 may determine that the number of iterations is not satisfied, and may determine to perform a next iteration for extracting a representative waveform. In another example, the processor 120 may calculate a similarity between the representative waveform extracted in the current iteration and a representative waveform extracted in a previous iteration, and if the calculated similarity is greater than or equal to a predetermined threshold value, the processor 120 may determine that the number of iterations is satisfied, and if the calculated similarity is less than the predetermined threshold value, the processor 120 may determine that the number of iterations is not satisfied and may determine to perform the next iteration for extracting a representative waveform. In yet another example, if a difference between quality evaluation results of the respective sub-signals in the current iteration and quality evaluation results of the respective sub-signals in the previous iteration, e.g., a difference between a statistical value (e.g., mean value, median value, etc.) of the quality evaluation results of the sub-signals in the current iteration and a statistical value of the quality evaluation results of the sub-signals in the previous iteration is less than or equal to a predetermined threshold value, the processor 120 may determine that number of iterations for extracting the representative waveform is satisfied, and if the difference exceeds the predetermined threshold value, the processor 120 may determine that the number of times of iteration for extracting the representative waveform is not satisfied, and may determine to perform the next iteration. However, the determination is not limited thereto.

Subsequently, upon determining to perform the next iteration based on the determination in operations 935 that the number of iterations for extracting the representative waveform is not satisfied, the processor 120 may adjust weights to be applied to the respective sub-signals in the next iteration in 940. Then, by performing operations 925 and 930 again, the processor 120 may apply the adjusted weights to the respective sub-signals, and then by overlapping the weighted sub-signals, the processor 120 may extract a new representative waveform, and may evaluate the quality of the respective sub-signals based on the extracted representative waveform.

For example, based on the quality evaluation results of the respective sub-signals which are calculated in the current iteration of operation 930, the processor 120 may adjust weights for the respective sub-signals. For example, the processor 120 may set a greater weight for high quality sub-signals. In addition, the processor 120 may set a weight of sub-signals, having quality values less than or equal to a predetermined level, to zero. In this manner, sub-signals having quality values less than or equal to a reference value may be excluded from a group of sub-signals used for generating a next representative waveform. For example, in the case where a signal quality of an ith sub-signal is defined as $Q_i$ in which $Q_i$ has values from 0 to 1, if the $Q_i$ has a value less than 0.5, a weight $W_i$ may be calculated as shown in the following Equation 1 in order to set the weight to zero.

$$W_i = 0, \text{ if } Q_i < 0.5$$

$$W_i = 2*(Q_i - 0.5), \text{ else} \qquad \text{[Equation 1]}$$

In another embodiment, as shown in Equation 2, the processor 120 may set quality values of the respective sub-signals as weights to be applied to corresponding sub-signals. However, the example of adjusting the weights is not limited thereto.

$$W_i = Q_1 \qquad \text{[Equation 2]}$$

Once the weights of the respective sub-signals are changed, a representative waveform obtained by a weighted overlapping of the sub-signals may also be changed. When the representative waveform is changed, the qualities of the respective sub-signals, which are calculated based on a similarity to the representative waveform, is also changed. Accordingly, the representative waveform may be extracted repeatedly by evaluating the quality of the sub-signals, adjusting the weights of the respective sub-signals, and weighted overlapping of the respective sub-signals.

Then, if a number of times of iteration is satisfied, the processor 120 may evaluate the quality of the extracted representative waveform in operations 945.

For example, the processor 120 may evaluate the quality of the extracted representative waveform based on evaluation results of the qualities of the respective sub-signals which are evaluated in 930. For example, the processor 120 may calculate a statistical value, such as an average, standard deviation, variance, coefficient of variation, etc., of quality values of the respective sub-signals, and may evaluate the signal quality of the extracted representative waveform based on the calculated statistical value. For example, the processor 120 may determine the calculated statistical value itself or a value, obtained by applying a predefined model, as the signal quality value of the corresponding representative waveform.

Subsequently, based on the evaluation result, the processor 120 may determine whether the representative waveform satisfies a predetermined quality criterion in operation 950, and if the representative waveform satisfies the predetermined quality criterion, the processor 120 may determine the representative waveform as a final representative waveform in operation 955. For example, if the quality of the representative waveform is greater than or equal to a predetermined threshold value (e.g., an average of the qualities of the sub-signals being 0.65), the processor 120 may determine that the quality is good and may determine the representative waveform as a final representative waveform. If the quality of the representative waveform does not satisfy the predetermined quality criterion, the processor 120 repeats operation 910 of receiving an input of a bio-signal, in which by excluding some of the sub-signals selected during the previous iteration, the processor 120 may select sub-signals including some of new sub-signals divided during the current iteration. For example, the processor 120 may exclude some of the sub-signals in time sequential order or in order starting from the lowest quality among the sub-signals in the previous iteration.

For example, if the generated representative waveform does not satisfy a quality criterion based on a predetermined number of sub-signals or sub-signals in a predetermined time interval, the processor 120 may further acquire one periodic signal and may generate a representative waveform again. In this case, the processor 120 may select sub-signals for use in generating a representative waveform from among the predetermined number of existing sub-signals or the existing sub-signals in the predetermined time interval, and newly acquired sub-signals. In one embodiment, by excluding a first sub-signal, which is first measured using First-In First-Out (FIFO), and by adding a newly acquired sub-signal, the processor 120 may select sub-signals to be overlapped. In another embodiment, the processor 120 may evaluate a signal quality of the selected sub-signals, and by excluding a sub-signal having the lowest signal quality, and by adding a newly measured sub-signal, the processor 120 may select a sub-signal to be overlapped.

Referring back to FIG. 1, the processor 120 may estimate bio-information based on the determined final representative waveform. In this case, the bio-information may include blood pressure, arrhythmia, vascular age, skin elasticity, skin age, arterial stiffness, aortic pressure waveform, stress index, fatigue level, etc., but is not limited thereto.

For example, the processor 120 may extract one or more features from the determined final representative waveform. For example, the processor 120 may extract, as features, amplitude and/or time values associated with propagation waves and reflection waves. Alternatively, the processor 120 may extract, as features, shape of a waveform, time and/or amplitude values at a maximum point during a systolic phase of the waveform, time and/or amplitude values at a minimum point, a total or partial area of the waveform, elapsed time, and the like. However, these are merely examples.

The processor 120 may estimate bio-information by combining one or two or more of the extracted features and by using a predefined bio-information estimation model. The bio-information estimation model may be predefined by using various methods, such as a linear function equation, nonlinear regression analysis, neural network, deep learning, and the like.

Figure 10:
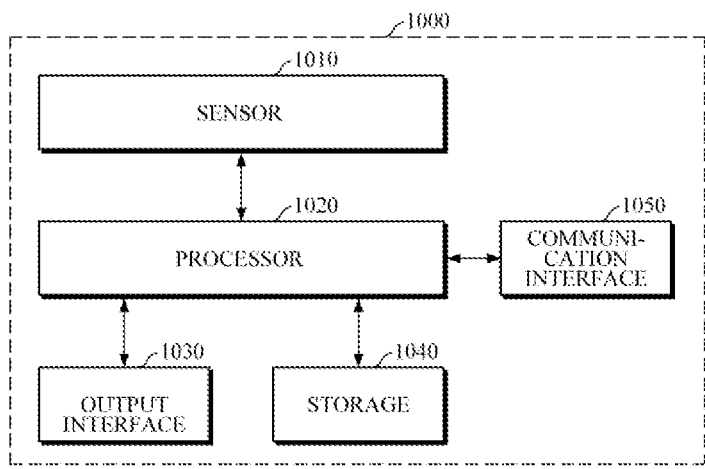
FIG. 10 is a block diagram of an apparatus for estimating bio-information according to an embodiment.

FIG. 10 is a block diagram of an apparatus for estimating bio-information according to an embodiment.

Referring to FIG. 10, the apparatus 1000 for estimating bio-information may include a sensor 1010, a processor 1020, an output interface 1030, a storage 1040, and a communication interface 1050. In this case, various embodiments of the sensor 1010 and the processor 1020 are described above with reference to FIGS. 1 to 9, such that a description thereof will be omitted.

The output interface 1030 may provide processing results of the processor 1020 to user. For example, the output interface 1030 may display an estimated bio-information value of the processor 1020 on a display. In this case, if the estimated bio-information value falls outside a normal range, the output interface 1030 may provide the user with warning information by changing color, line thickness, etc., or displaying an abnormal value along with a normal range, so that the user may easily recognize the abnormal value. Further, the output interface 1030 may provide the user with the estimated bio-information value in a non-visual manner by voice, vibrations, tactile sensation, and the like using an audio output module such as a speaker, or a haptic module and the like.

In addition, the output interface 1030 may visually display processes of estimating bio-information performed by the processor 1020 and bio-information estimation results in graphs. Further, if the quality of a bio-signal is not good, the output interface 1030 may guide a user to re-measure a bio-signal or to additionally measure the bio-signal, or may terminate estimating the bio-signal.

The storage 1040 may store information related to estimating bio-information. For example, the storage 1040 may store the bio-signal, acquired by the sensor 1010, and the processing results of the processor 1020, e.g., the representative waveform determination result and the estimated bio-information value. Further, the storage 1040 may store a bio-information estimation model, a threshold value used for determining a representative waveform, user characteristic information, and the like. In this case, the user characteristic information may include a user's age, gender, health condition, and the like.

The storage 1040 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EE-PROM), a Programmable Read Only Memory (PROM), a magnetic memory, a magnetic disk, and an optical disk, and the like, but is not limited thereto.

The communication interface 1050 may communicate with an external device to transmit and receive various data related to estimating bio-information. The external device may include an information processing device such as a smartphone, a tablet PC, a desktop computer, a laptop computer, and the like. For example, the communication interface 1050 may transmit a bio-information estimation result to the external device, such as a user's smartphone and the like, so that the user may manage and monitor component analysis results using a device having a relatively high performance. In addition, in the case where the external device includes a sensor for measuring a bio-signal, the communication interface 1050 may receive a bio-signal from the external device.

The communication interface 1050 may communicate with the external device by using various wired or wireless communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G, 4G, and 5G communications, and the like. However, this is merely exemplary and is not intended to be limiting.

Figure 11:
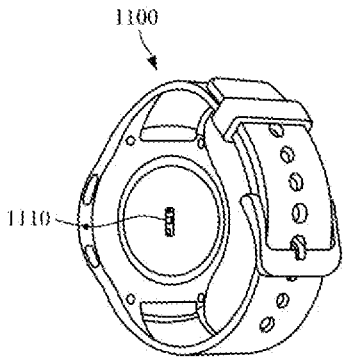
FIG. 11 is a diagram of a wristwatch wearable electronic device for estimating bio-information according to an embodiment.
Figure 12:
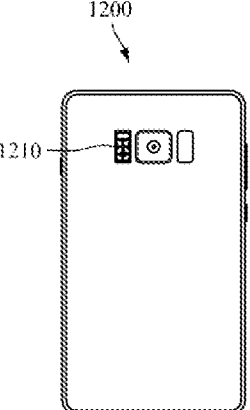
FIG. 12 is a diagram of a mobile electronic device for estimating bio-information according to an embodiment.
Figure 13:
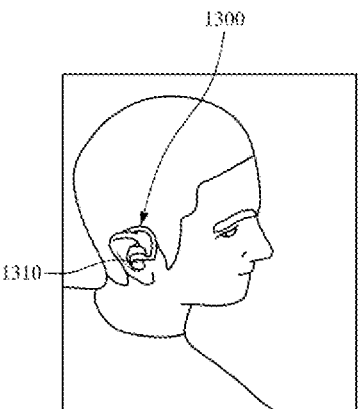
FIG. 13 is a diagram of an ear-wearable electronic device for estimating bio-information according to an embodiment.

FIGS. 11 to 13 are diagrams showing various structures of an electronic device including the apparatus 100 or 1000 for estimating bio-information of FIG. 1 or FIG. 10 according to embodiments.

The electronic device may include, for example, various types of wearable devices, e.g., a smart watch, a smart band, smart glasses, smart earphones, a smart ring, a smart patch, and a smart necklace, and a mobile device such as a smartphone, a tablet PC, etc., or home appliances or various Internet of Things (IoT) devices (e.g., home IoT device, etc.) based on Internet of Things (IoT) technology.

The electronic device may include a sensor device, a processor, an input device, a communication module, a camera module, an output device, a storage device, and a power module. All the components of the electronic device may be integrally mounted in a specific device or may be distributed in two or more devices. The sensor device may include the sensor (e.g., PPG sensor) of the apparatuses 100 and 1000 for estimating bio-information, and may further include an additional sensor, such as a gyro sensor, a Global Positioning System (GPS), and the like.

The processor may execute programs, stored in the storage device, to control components connected to the processor, and may perform various data processing or computation, including estimation of bio-information (e.g., blood pressure). For example, the processor may determine a representative waveform of a PPG signal measured by using a PPG sensor of the sensor device, and may estimate blood pressure based on the determination result. Various examples of determining the representative waveform and estimating blood pressure are described above, such that a detailed description thereof will be omitted. The processor may include a main processor, e.g., a central processing unit (CPU) or an application processor (AP), etc., and an auxiliary processor, e.g., a graphics processing unit (GPU), an image signal processor (ISP), a sensor hub processor, or a communication processor (CP), etc., which is operable independently from, or in conjunction with, the main processor.

The input device may receive a command and/or data to be used by each component of the electronic device, from a user and the like. The input device may include, for example, a microphone, a mouse, a keyboard, or a digital pen (e.g., a stylus pen, etc.).

The communication module may support establishment of a direct (e.g., wired) communication channel and/or a wireless communication channel between the electronic device and other electronic device, a server, or the sensor device within a network environment, and performing of communication via the established communication channel. The communication module may include one or more communication processors that are operable independently from the processor and supports a direct communication and/or a wireless communication. The communication module may include a wireless communication module, e.g., a cellular communication module, a short-range wireless communication module, or a global navigation satellite system (GNSS) communication module, etc., and/or a wired communication module, e.g., a local area network (LAN) communication module, a power line communication (PLC) module, and the like. These various types of communication modules may be integrated into a single chip, or may be separately implemented as multiple chips. The wireless communication module may identify and authenticate the electronic device in a communication network by using subscriber information (e.g., international mobile subscriber identity (IMSI), etc.) stored in a subscriber identification module.

The camera module may capture still images or moving images. The camera module may include a lens assembly having one or more lenses, image sensors, image signal processors, and/or flashes. The lens assembly included in the camera module may collect light emanating from a subject to be imaged.

The output device may visually/non-visually output data generated or processed by the electronic device. The output device may include a sound output device, a display device, an audio module, and/or a haptic module.

The sound output device may output sound signals to the outside of the electronic device. The sound output device may include a speaker and/or a receiver. The speaker may be used for general purposes, such as playing multimedia or playing record, and the receiver may be used for incoming calls. The receiver may be implemented separately from, or as part of, the speaker.

The display device may visually provide information to the outside of the electronic device. The display device may include, for example, a display, a hologram device, or a projector and control circuitry to control the devices. The display device may include touch circuitry adapted to detect a touch, and/or sensor circuitry (e.g., pressure sensor, etc.) adapted to measure the intensity of force incurred by the touch.

The audio module may convert a sound into an electrical signal or vice versa. The audio module may obtain the sound via the input device, or may output the sound via the sound output device, and/or a speaker and/or a headphone of another electronic device directly or wirelessly connected to the electronic device.

The haptic module may convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

The storage device may store driving conditions required for driving the sensor device, and various data required for other components of the electronic device. The various data may include, for example, software and input data and/or output data for a command related thereto. The storage device may include a volatile memory and/or a non-volatile memory.

The power module may manage power supplied to the electronic device. The power module may be implemented as least part of, for example, a power management integrated circuit (PMIC). The power module may include a battery, which may include a primary cell which is not rechargeable, a secondary cell which is rechargeable, and/or a fuel cell.

Referring to FIG. 11, the electronic device may be implemented as a wristwatch wearable device 1100, and may include a main body and a wrist strap. A display may be provided on a front surface of the main body, and may display various application screens, including time information, received message information, and the like. A sensor device 1110 may be disposed on a rear surface of the main body.

Referring to FIG. 12, the electronic device may be implemented as a mobile device 1200 such as a smartphone.

The mobile device 1200 may include a housing and a display panel. The housing may form an exterior of the mobile device 1200. The housing may have a first surface, on which a display panel and a cover glass may be disposed sequentially, and the display panel may be exposed to the outside through the cover glass. The sensor device 1110, a camera module and/or an infrared sensor, and the like may be disposed on a second surface of the housing. The processor and various other components may be disposed in the housing.

Referring to FIG. 13, the electronic device may be implemented as an ear-wearable device 1300.

The ear-wearable device 1300 may include a main body and an ear strap. A user may wear the ear-wearable device 1300 by hanging the ear strap on the auricle. The ear strap may be omitted depending on a shape of the ear-wearable device 1300. The main body may be inserted into the external auditory meatus. A sensor device 1310 may be mounted in the main body. Further, the processor may be disposed in the main body, and may estimate blood pressure by using a pulse wave signal measured by the sensor device 1310. Alternatively, the ear-wearable device 1300 may estimate blood pressure by interworking with an external device. For example, the pulse wave signal, measured by the sensor device 1310 of the ear-wearable device 1300, may be transmitted to an external device, e.g., a mobile device, a tablet PC, etc., through a communication module provided in the main body, so that a processor of the external device may estimate blood pressure, and the estimated blood pressure value may be output through a sound output module provided in the main body of the ear-wearable device 1300.

Embodiments can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the present disclosure can be readily deduced by programmers of ordinary skill in the art to which the disclosure pertains.

The present disclosure has been described herein with regard to example embodiments. However, it will be obvious to those skilled in the art that various changes and modifications can be made without changing technical conception and essential features of the present disclosure. Thus, it is clear that the above-described embodiments are illustrative in all aspects and are not intended to limit the present disclosure.

What is claimed is:

1. A method of extracting a representative waveform of a bio-signal, the method comprising:
   measuring, using a sensor, the bio-signal of an object;
   dividing the bio-signal into a plurality of sub-signals;
   selecting at least one sub-signal for extracting a target waveform from among the plurality of sub-signals;
   extracting the target waveform from the bio-signal by using the at least one selected sub-signal;
   evaluating a quality of the target waveform;

based on the target waveform satisfying a predetermined quality criterion corresponding to the evaluation, determining that the target waveform is the representative waveform; and
   estimating bio-information of the object based on the representative waveform, the bio-information comprising a blood pressure, an arrhythmia, a vascular age, an arterial stiffness, an aortic pressure waveform, and a fatigue level,
   wherein the extracting of the target waveform comprises setting first weights of first sub-signals from the at least one selected sub-signal having a first quality that meets or exceeds a predetermined quality threshold based on a difference between the first quality and the predetermined quality threshold, and clearing second weights of second sub-signals from the at least one selected sub-signal having a second quality that does not meet the predetermined quality threshold.

2. The method of claim 1, wherein the dividing of the bio-signal into the plurality of sub-signals comprises dividing the bio-signal into the plurality of sub-signals based on units of beats.

3. The method of claim 1, wherein the selecting of the at least one sub-signal comprises selecting a predetermined number of sub-signals or sub-signals in a predetermined time interval.

4. The method of claim 1, wherein the selecting of the at least on sub-signal comprises selecting a plurality of selected sub-signals;
   wherein the extracting of the target waveform comprises:
      setting a reference point in each of the plurality of selected sub-signals; and
      overlapping the plurality of selected sub-signals based on the reference point in each of the plurality of selected sub-signals.

5. The method of claim 4, wherein the setting of the reference point comprises setting, as the reference point, at least one of a minimum point of a waveform of each of the plurality of selected sub-signals, a maximum point of the waveform of each of the plurality of selected sub-signals, a maximum slope point of the waveform of each of the plurality of selected sub-signals, or a tangent intersection point of the waveform of each of the plurality of selected sub-signals.

6. The method of claim 4, wherein the overlapping of the plurality of selected sub-signals comprises overlapping the plurality of selected sub-signals after normalizing the plurality of selected sub-signals to a same size.

7. The method of claim 1, wherein the selecting of the at least on sub-signal comprises selecting a plurality of selected sub-signals, and
   wherein the extracting of the target waveform comprises extracting the target waveform by applying weights to the plurality of selected sub-signals, and then overlapping the weighted plurality of selected sub-signals.

8. The method of claim 7, wherein the extracting of the target waveform comprises:
   in response to the target waveform being extracted, determining whether a number of iterations is satisfied;
   based on the number of iterations not being satisfied, adjusting the weights;
   extracting a new target waveform by applying the adjusted weights to the plurality of selected sub-signals; and
   overlapping the plurality of selected sub-signals having the adjusted weights.

9. The method of claim 8, wherein the determining whether the number of iterations is satisfied comprises:

determining that the number of iterations is satisfied based on a first difference between a representative waveform in a current iteration and a representative waveform in a previous iteration being less than or equal to a first predetermined threshold value; and determining that the number of iterations is satisfied based on a second difference between a quality evaluation result of the plurality of selected sub-signals in the current iteration and a quality evaluation result of the plurality of selected sub-signals in the previous iteration being less than or equal to a second predetermined threshold value.

10. The method of claim 8, wherein the extracting of the target waveform further comprises evaluating a quality of the plurality of selected sub-signals, and wherein the adjusting of the weights comprises adjusting the weights based on the quality evaluation result of the plurality of selected sub-signals.

11. The method of claim 1, further comprising, based on the target waveform not satisfying the predetermined quality criterion, repeating the measuring of the bio-signal, wherein the selecting of the at least one sub-signal comprises excluding some sub-signals selected during a previous iteration, and including some new sub-signals divided during current iteration.

12. The method of claim 11, wherein the selecting of the at least one sub-signal comprises:

sorting the plurality of sub-signals in the previous iteration based on at least one of a time sequential order or a descending quality order; and excluding one or more sub-signals from among a bottom of the sorted plurality of sub-signals.

13. The method of claim 11, wherein the selecting of the at least one sub-signal comprises excluding a first measured sub-signal and adding a newly acquired sub-signal using First-In First-Out (FIFO).

14. The method of claim 11, wherein the selecting of the at least one sub-signal comprises:

determining a signal quality of each of the at least one sub-signal;

excluding a sub-signal having a lowest signal quality from among the at least one sub-signal; and adding a newly measured sub-signal to the at least one sub-signal.

15. An apparatus for estimating bio-information, the apparatus comprising:

a sensor configured to measure a bio-signal from an object; and a processor configured to:

divide the bio-signal into a plurality of sub-signals;

select at least one sub-signal for extracting a target waveform from among the plurality of sub-signals;

extract the target waveform from the bio-signal by using the at least one selected sub-signal;

evaluate a quality of the target waveform;

based on the target waveform satisfying a predetermined quality criterion corresponding to the evaluation, determine that the target waveform is a representative waveform of the bio-signal; and estimate the bio-information of the object based on the representative waveform, the bio-information comprising a blood pressure, an arrhythmia, a vascular age, an arterial stiffness, an aortic pressure waveform, and a fatigue level, wherein the processor is configured to:

set first weights of first sub-signals from the at least one selected sub-signal having a first quality that meets or exceeds a predetermined quality threshold based on a difference between the first quality and the predetermined quality threshold, and clear second weights of second sub-signals from the at least one selected sub-signal having a second quality that does not meet the predetermined quality threshold.

16. The apparatus of claim 15, wherein the at least one selected sub-signal comprises a plurality of selected sub-signals, and wherein the processor is further configured to:

set a reference point in each of the plurality of selected sub-signals, and extract the target waveform by overlapping the plurality of selected sub-signals based on the reference point in each of the plurality of selected sub-signals.

17. The apparatus of claim 16, wherein the processor is further configured to set, as the reference point, at least one of a minimum point of a waveform of each of the plurality of selected sub-signals, a maximum point of the waveform of each of the plurality of selected sub-signals, a maximum slope point of the waveform of each of the plurality of selected sub-signals, or a tangent intersection point of the waveform of each of the plurality of selected sub-signals.

18. The apparatus of claim 16, wherein the processor is further configured to overlap the plurality of selected sub-signals after normalizing the plurality of selected sub-signals to a same size.

19. The apparatus of claim 15, wherein the at least one selected sub-signal comprises a plurality of selected sub-signals, and wherein the processor is further configured to extract the target waveform by applying weights to the plurality of selected sub-signals, and overlapping the weighted plurality of selected sub-signals.

20. The apparatus of claim 16, wherein upon extracting the target waveform, the processor is further configured to:

determine whether a number of iterations is satisfied;

in response to the number of iterations not being satisfied, adjust weights applied to the plurality of selected sub-signals;

extract a new target waveform by applying the adjusted weights to the plurality of sub-signals; and overlap the plurality of sub-signals having the adjusted weights.

21. The apparatus of claim 20, wherein the processor is further configured to:

determine that the number of iterations is satisfied based on a predetermined number of times of iteration is satisfied;

determine that the number of iterations is satisfied based on a first difference between a representative waveform in a current iteration and a representative waveform in a previous iteration being less than or equal to a first predetermined threshold value; and determine that the number of iterations is satisfied based on a second difference between a quality evaluation result of the at least one selected sub-signal in the current iteration and a quality evaluation result of the at least one selected sub-signal in the previous iteration being less than or equal to a second predetermined threshold value.

22. The apparatus of claim 20, wherein the processor is further configured to evaluate a quality of the at least one selected sub-signal, and adjusts the weights based on a quality evaluation result of the at least one selected sub-signal.

23. The apparatus of claim 15, wherein based on the target waveform not satisfying the predetermined quality criterion, the processor is further configured to repeatedly measure the bio-signal, and wherein the processor is further configured to exclude some sub-signals selected during a previous iteration, and to include some new sub-signals divided during a current iteration.

24. A method of extracting a representative waveform of a bio-signal, the method comprising:

measuring, using a sensor, a first bio-signal of an object;

dividing the first bio-signal into a plurality of sub-signals;

selecting a plurality of selected sub-signals for extracting a target waveform from among the plurality of sub-signals;

extracting the target waveform from the bio-signal by using the plurality of selected sub-signals;

evaluating a quality of the target waveform;

based on the target waveform satisfying a predetermined quality criterion corresponding to the evaluation, determining that the target waveform is the representative waveform of the bio-signal;

based on the target waveform not satisfying the predetermined quality criterion corresponding to the evaluation:

measuring, using the sensor, a second bio-signal;

selecting a sub-signal from the second bio-signal; and extracting the target waveform by using the plurality of selected sub-signals and the sub-signal from the second bio-signal; and estimating bio-information of the object based on the representative waveform, the bio-information comprising a blood pressure, an arrhythmia, a vascular age, an arterial stiffness, an aortic pressure waveform, and a fatigue level, wherein the extracting of the target waveform comprises setting first weights of first sub-signals from the at least one selected sub-signal having a first quality that meets or exceeds a predetermined quality threshold based on a difference between the first quality and the predetermined quality threshold, and clearing second weights of second sub-signals from the at least one selected sub-signal having a second quality that does not meet the predetermined quality threshold.

* * * * *